United States Patent [19]
Rognan et al.

[11] Patent Number: 5,498,628
[45] Date of Patent: Mar. 12, 1996

[54] NAPHTHAMIDE DERIVATIVES

[75] Inventors: Didier Rognan, Saint Louis; Andre Mann, Ostwald; Camille-Georges Wermuth, Strasbourg; Marie-Pascale Martres, Paris; Bruno Giros, Chatillon; Pierre Sokoloff, Le Plessis Bouchard; Jean-Charles Schwartz; Jeanne-Marie LeComte, both of Paris; Fabrice Garrido, Strasbourg, all of France

[73] Assignee: Institut National de la Sante et de la Recherche Medicale, Paris, France

[21] Appl. No.: 965,927

[22] Filed: Oct. 23, 1992

[30] Foreign Application Priority Data

Oct. 23, 1991 [FR] France .................... 91 13103

[51] Int. Cl.⁶ .................... A61K 31/40; C07D 207/09
[52] U.S. Cl. .................... 514/428; 548/567
[58] Field of Search .................... 548/567; 514/428

[56] References Cited

FOREIGN PATENT DOCUMENTS 0393838 10/1990 European Pat. Off. .

OTHER PUBLICATIONS

Banitt et al., J. Med. Chem., vol. 18 (1975) pp. 1/30–1/34.
J. Med Chem. 1990, 1989 American Chemical Society, "Synthesis and Characterization of Iodobenzamide Analogues . . . ".

*Primary Examiner*—Robert W. Ramsuer
*Attorney, Agent, or Firm*—Larson and Taylor

[57] ABSTRACT

The new naphthamide derivatives according to the invention are characterized in that they correspond to the general formula (I),

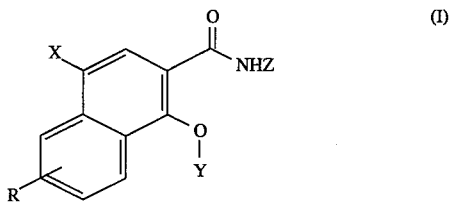

where
X: represents either a hydrogen atom, or a chlorine or bromine atom, or an amino or aminoalkyl group, an aminosulphamoyl group, a sulphur-containing group such as thiocyanate, alkylthio, alkylsulphinyl or alkylsulphonyl, or a methoxy group, or a nitro group, or a cyano group, or an electron-attracting group;

Y: represents an alkyl or alkenyl residue;

Z: represents the residues originating from 2-aminomethyl-N-alkylpyrrolidine, 2-aminoethyl-N,N-diethylamine, 2-(aminoethyl)morpholine, 2-aminoethyl-N,N-dibutylamine, 4-amino-N-butylpiperidine or 2-(aminoethyl)pyrrolidine;

R: a hydrogen or an $OCH_3$ substituent.

These new derivatives may be employed in the preparation of medicinal products intended for use as an antipsychotic, psychostimulatory, anti-autistic or antidepressant agent, an agent for treating Parkinson's disease or an antihypertensive agent.

7 Claims, No Drawings

NAPHTHAMIDE DERIVATIVES

The present invention relates to new naphthamide derivatives, to a process for preparing them and to their application in the therapeutic field.

Many benzamide derivatives, in particular orthomethoxybenzamide derivatives, are known and used for their activities with respect to the central nervous system, especially for their neuroleptic qualities (Justin-Besancon et al., C. R. Acad. Sci. Paris, 1964, 265:1253–1254; Jonner and Marsden, Life Sci. 1979, 25:479–486).

In contrast, the corresponding 1-methoxynaphtamide derivatives have not been described in the literature. Now, the Applicant has discovered that, surprisingly, the 1-methoxynaphtamide derivatives of general formula (1) given below are characterised by a stronger affinity for dopaminergic receptors than that of the benzamides known hitherto. Furthermore, these new derivatives display some power of discrimination between receptors of the subclass $D_2$ and those of the subclass $D_3$ (Sokoloff et al. Nature 1990, 347: 146–151). The preferential affinity for $D_3$ receptors displayed by the new naphthamide derivatives according to the invention allows of a neuroleptic therapy free from extrapyramidal syndromes.

The new naphthamide derivatives according to the invention are characterised in that they correspond to the general formula (I),

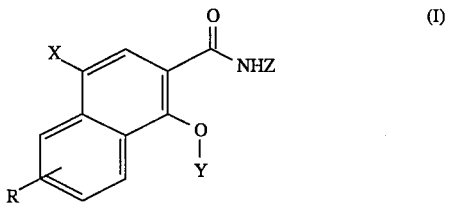

where
X: represents either a hydrogen atom, or a chlorine or bromine atom, or an amino or aminoalkyl group, an aminosulphamoyl group, a sulphur-containing group such as thiocyanate, alkythio, alkylsulphinyl or alkylsulphonyl, or a methoxy group, or a nitro group, or a cyano group, or an electron-attracting group;

Y: represents an alkyl or alkenyl residue;

Z: represents the residues originating from 2-aminomethyl-N-alkylpyrrolidine, 2-aminoethyl-N,N-diethylamine, 2 (aminoethyl)morpholine, 2-aminoethyl-N,N-dibutylamine, 4-amino-N-butyl (or benzyl) piperidine or 2-(aminoethyl)pyrrolidine;

R: a hydrogen or an $OCH_3$ substituent.

According to an embodiment, the compounds can correspond to the formula

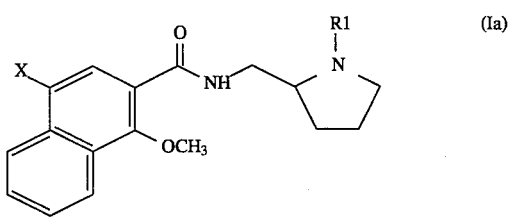

where X represents a hydrogen atom, a halogen atom such as chlorine or bromine, an amino or aminoalkyl group, an aminosulphamoyl group, a lower alkoxy group such as a methoxy group, a nitro group or alternatively a cyano group, R1 represents a lower alkyl group, a lower cycloalkylalkyl group, an aralkyl group such as a phenylalkyl group or alternatively an allyl group.

The present invention also relates to the addition salts formed by the compounds of formula (I, Ia) with physiologically acceptable acids such as hydrochloric, sulphuric, nitric, maleic, and the like, acids.

Lower alkyl is understood to mean a linear or branched alkyl radical containing 1 to 6 carbon atoms, and more especially methyl, ethyl, propyl and butyl radicals.

Preferred compounds of the invention are, more especially, those which correspond to the general formula (I, Ia) in which X represents a hydrogen atom, a chlorine or fluorine atom, an amino, nitro or cyano group or alternatively a methoxy group; and R1 represents an ethyl, propyl or butyl radical, a benzyl group or a lower cycloalkylalkyl group such as a cyclopropylmethyl group, or alternatively an allyl group.

The compounds of formula (I) according to the invention possess an asymmetric carbon atom, and can hence take the form of racemates or optical isomers, which also form part of the invention.

Among the more especially preferred compounds, the following compounds may be mentioned:

N-[N-1-Butyl-2-pyrrolidinyl)methyl]-1methoxy-4-bromo-2-naphthamide, optionally in hydrochloride form, N-[(N-Allyl-2-pyrrolidinyl)methyl]-1-methoxy-4-cyano-2-naphthamide, N-[(N-Ethyl-2-pyrrolidinyl)methyl]-1-methoxy-2-naphthamide, 4-Amino-N-[(N-ethyl-2-pyrrolidinyl)methyl]-1-methoxy-2-naphthamide, optionally in dihydrochloride form, 4-Nitro-N[(N-ethyl-2-pyrrolidinyl)methyl]-1-methoxy-2-naphthamide, N-[(N-Ethyl-2-pyrrolidinyl)methyl]-1,4-dimethoxy-2-naphthamide, optionally in hydrochloride form, 4-Chloro-N-[(N-ethyl-2-pyrrolidinyl)mothyl]-1-methoxy-2-naphthamide, optionally in hydrochloride form, 4-Bromo-N-[(N-ethyl-2-pyrrolidinyl)methyl]-1-methoxy-2-naphthamide, optionally in hydrochloride form, 4-Methylsulphonylamino-N-[(N-ethyl-2-pyrrolidinyl)methyl]-1-methoxy-2-naphthamide, optionally in hydrochloride form, N-[(N-Benzyl-2-pyrrolidinyl)methyl]-1-methoxy-2-naphthamide, optionally in hydrochloride form, 4-Nitro-N-[(N-benzyl-2-pyrrolidinyl)methyl]-1-methoxy-2-naphthamide, 4-Chloro-N-[(N-benzyl-2-pyrrolidinyl)methyl]-1-methoxy-2-naphthamide, 4-Chloro-N-[(N-propyl-2-pyrrolidinyl)methyl]-1-methoxy-2-naphthamide, 4-Bromo-N-[(N-cyclopropylmethyl-2-pyrrolidinyl)methyl]-1-methoxy-2-naphthamide, 4-Chloro-N-[(N-allyl-2-pyrrolidinyl)methyl]-1-methoxy-2-naphthamide, 4-Nitro-N-[(N-allyl-2-pyrrolidinyl)methyl]-1-methoxy-2-naphthamide, 4-Cyano-N-[(N-ethyl-2-pyrrolidinyl)methyl]-1-methoxy-2-naphthamide, 4-Cyano-N-[(N-butyl-2-pyrrolidinyl)methyl]-1-methoxy-2-naphthamide 4-Cyano-N-{[N-(3-butenyl)-2-pyrrolidinyl]-methyl}-1-methoxy-2-naphthamide, 4-Cyano-N-[(N-pentyl-2-pyrrolidinyl)methyl]-1-methoxy-2-naphthamide, 4-Cyano-N-{[N-(4-pentenyl)-2-pyrrolidinyl]methyl}-1-methoxy-2-naphthamide, 1,5-Dimethoxy-N-[(N-ethyl-2-pyrrolidinyl)methyl]-2-naphthamide hydrochloride, 1,5-Dimethoxy-N[(N-butyl-2-pyrrolidinyl)methyl]-2-naphthamide hydrochloride, 4-Bromo-N-[(N,N-diethylamino)ethyl]-1-methoxy-2-naphthamide,
4-Bromo-N-[(morpholino)ethyl]-1-methoxy-2-naphthamide,
4-Bromo-N-(N-butyl-4-piperidyl)-1-methoxy-2-naphthamide,
4-Bromo-N-(N-benzyl-4-piperidyl)-1-methoxy-2-naphthamide,
4-Nitro-N-[(morpholino)ethyl]-1-methoxy-2-naphthamide,
4-Nitro-N-[(N-butyl-2-pyrrolidinyl)methyl]-1,5-dimethoxy-2-naphthamide hydrochloride,
4-Nitro-N-(N-butyl-4-piperidyl)-1-methoxy-2-naphthamide,
4-Nitro-N-[(N,N-diethylamino)ethyl]-1-methoxy-2-naphthamide,
4-Bromo-N-[(N,N-dibutylamino)ethyl]-1-methoxy-2-naphthamide hydrochloride,
4-Bromo-N-[(N-ethyl-2-pyrrolidinyl)methyl]-1-butoxy-2-naphthamide,
4-Nitro-N-[(N-ethyl-2-pyrrolidinyl)methyl]-1,5-dinitro-2-naphthamide,
4-Bromo-N-(N-butyl-4-piperidyl)-1-allyloxy-2-naphthamide,
4-Bromo-N-[(morpholino)ethyl]-1-allyloxy-2-naphthamide hydrochloride,
1,4-Dimethoxy-N-(N-butyl-4-piperidyl)-2-naphthamide hydrochloride,
4-Bromo-N-[(morpholino)ethyl]-1-butoxy-2-naphthamide hydrochloride,
4-Bromo-N-[(N-ethyl-2-pyrrolidinyl)methyl]-1-cyclopentyloxy-2-naphthamide hydrochloride,
4-Nitro-N-[(N,N-dibutylamino)ethyl]-1-methoxy-2-naphthamide hydrochloride,
4-Bromo-N-[(2-pyrrolidinyl)ethyl]-1-methoxy-2-naphthamide,
4-Cyano-N-[(N,N-dibutylamino)ethyl]-1-methoxy-2-naphthamide hydrochloride.

The compounds of formula (I) according to the invention are obtained by processes of known type.

The appropriately substituted (1-methoxy-4-X-naphthoic) acid portion is converted to a mixed anhydride with ethyl chloroformate in acetone or any other solvent, in a basic medium, and reacted with the desired pyrrolidine as shown in the reaction scheme:

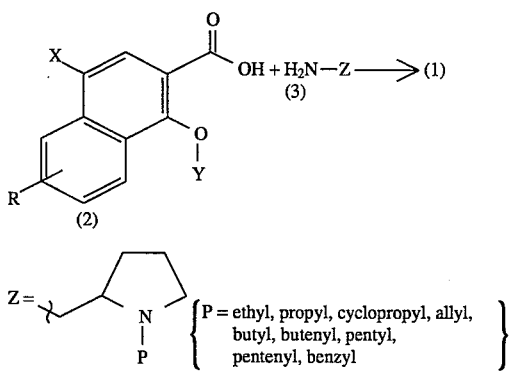

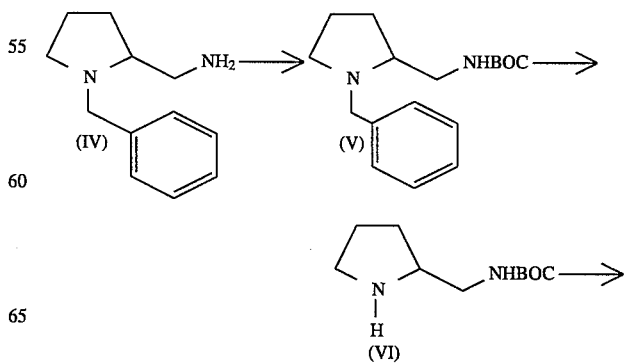

R = OCH$_3$, H

Other methods of activation of the carboxyl function may also be used; in fact, all methods of amide preparation are suitable, including the use of the acid chloride.

For R=OCH$_3$, the starting material was 1-hydroxy-5-methoxy-2-naphthoic acid, described in the literature (*J. Chem. Soc.*, 1937, 937).

The group X is introduced into the naphthoic acid either with bromine (X=Br), or by nitration (X=NO$_2$) and reduction (X=NH$_2$) and acylation (X=NHSO$_2$CH$_3$), or by a Sandmeyer reaction (X=Cl,CN).

For Y=alkyl, the starting material was 1-hydroxy-4-X-naphthoic acid, which was alkylated on the oxygen atom in a basic medium with an alkyl halide.

For X=OCH$_3$, the starting material was 1,4-dimethoxy-2-naphthoic acid. Moreover, the various amines used for obtaining the amide were obtained by the methods listed below:

From N-ethyl-2-(aminomethyl)pyrrolidine, 2-aminoethyl-N,N-diethylamine, 2-(aminoethyl)morpholine, 2-aminoethyl-N,N-dibutylamine, 2-(aminoethyl)pyrrolidine, which are commercially available.

From N-benzylpyrrolidine, according to the directions of Takashi and Masashi, Ger. Off. 1,941,536 (5th Mar. 1970).

From butyrolactone and an amine (propylamine, butylamine and cyclopropylamine), according to the directions of Kaplan, Ger. Off. 2,556,457 (24th Jun., 1976).

From (N-tert-butoxycarbonylaminomethyl)-N-benzylpyrrolidine (V) followed by debenzylation, alkylation with allyl bromide (or with bromo-1-butene or 5-bromo-1-pentene) and deprotection to obtain N-allyl

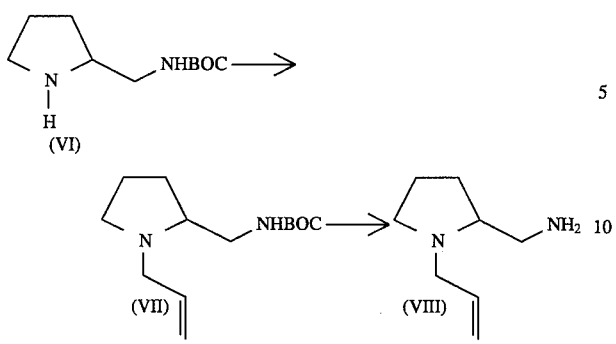

From N-benzyl-4-(N-tert-butoxycarbonylamino)-piperidine, by debenzylation followed by alkylation with an alkyl halide and by deprotection (see scheme) to obtain the amine XII.

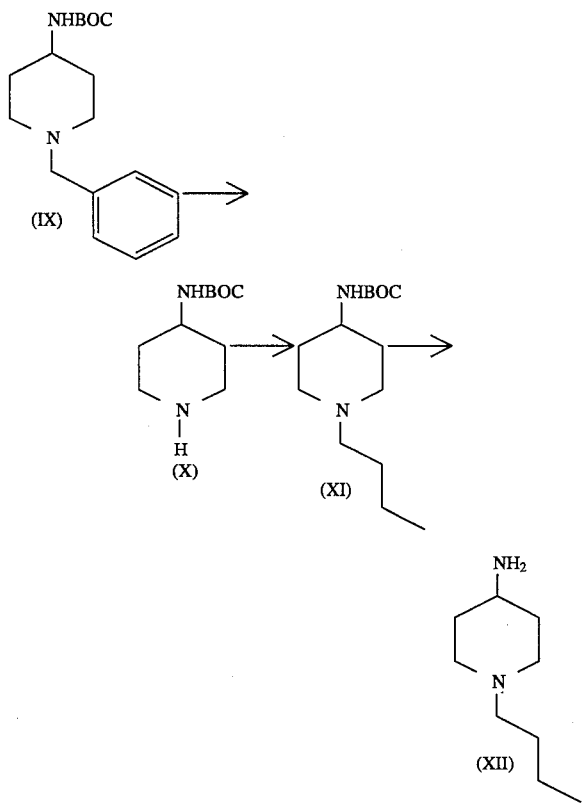

Thus the compounds of formula (Ia) may be obtained according to the following reaction scheme:

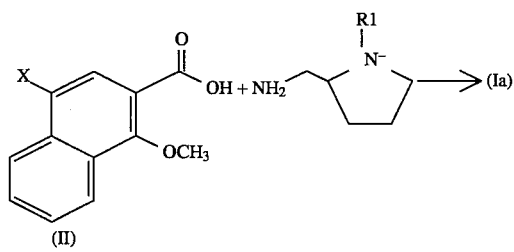

Other derivatives may be prepared by new processes, especially those in which R1 represents an allyl group.

The present invention hence also encompasses the process for preparing such derivatives, which are used as starting materials in the preparation of the naphthamide derivatives of formula (Ia) according to the present invention.

The process for preparing these derivatives is characterised in that, starting from the 2-(aminomethyl)pyrrolidine in which the heterocyclic nitrogen atom carries an aralkyl radical such as benzyl (Compound IV), it entails the steps:

- of protection of the primary amine, for example in the form of a carbamate (Compound V),
- of debenzylation of the heterocyclic nitrogen,
- of alkylation of the heterocyclic nitrogen with an alkyl halide such as an alkyl bromide,
- and then of deprotection of the primary amine, for example of the carbamate (Compound VI).

A few examples illustrating the implementation of the invention will be given below without implied limitation.

EXAMPLE 1

Preparation of N-[(N-1-butyl-2-pyrrolidinyl)methyl]-1-methoxy-4-bromo-2-naphthamide hydrochloride.

1. Preparation of 1-hydroxy-4-bromo-2-naphthoic acid methyl ester.

1.7 g (8.4 mmol) of 1-hydroxy-2-naphthoic acid methyl ester are introduced into a 100-ml round-bottomed flask, and 0.54 ml (10 mmol) of a solution of bromine in acetic acid is added dropwise. The mixture is stirred for 30 min at room temperature. It is diluted with water, the precipitate formed is filtered off and washed with water and 2.26 g of the compound of the title are recovered—M.p. 113° C. (Yield= 95%).

2. Preparation of 1-methoxy-4-bromo-2-naphthoic acid methyl ester.

A mixture consisting of 1-hydroxy-4-bromo-2-naphthoic naphthoic acid methyl ester (2.26 g, 8 mmol), potassium carbonate (1.6 g, 0.012 mol) and dimethyl sulphate (1.26 ml, 0.013 mol), all these ingredients being in acetone (50 ml), is heated to reflux overnight. The precipitate is filtered off and the acetone is evaporated off. The residue is taken up in ether, and the organic phase is washed with water, dried and evaporated to obtain 1.9 g of the compound of the title—M.p. 80° C. (Yield=80%).

3. Preparation of 1-methoxy-4-bromo-2-naphthoic acid.

1.8 g (6 mmol) of 1-methoxy-4-bromo-2-naphthoic acid methyl ester, obtained in 2, in 20 ml of methanol are heated to reflux for 48 h in the presence of 0.92 g (1.5 eq) of potassium bicarbonate. The solvent is evaporated off, the residue is taken up in water and the neutral substances are extracted with ether. The aqueous phase is then acidified with dilute hydrochloric acid. It is extracted with ethyl acetate, and the organic phase is washed with water, dried and concentrated to obtain 1.63 g of the acid of the title— M.p. 197° C. (Yield=95%).

4. Preparation of N-[(N-1-butyl-2-pyrrolidinyl)methyl]-1-methoxy-4-bromo-2-naphthamide hydrochloride.

281 mg (1 mmol) of 1-methoxy-4-bromo-2-naphthoic acid, obtained in 3, 0.17 ml (1.2 mmol) of triethylamine and 5 ml of acetone are introduced into a 25-ml round-bottomed flask. The mixture is cooled to −15° C. by means of an ice bath. 0.1 ml (1.05 mmol) of ethyl chloroformate dissolved in 2 ml of acetone is then added dropwise. The mixture is stirred for 30 min at −15° C. and 164 mg (1.05 mmol) of 2-aminomethyl-N-butylpyrrolidine are added. The reaction medium is allowed to return to room temperature, the precipitate obtained is filtered off and the filtrate is concentrated under vacuum. The residue is taken up in water and the mixture is then extracted with ethyl acetate (2×30 ml). The organic phase is washed with water, dried ($Na_2SO_4$) and concentrated. The residue is chromatographed on a silica column, using an ethyl acetate/methanol (85:15) mixture as eluent, to recover 310 mg of the compound of the title—M.p. 54° C. (Yield=74%).

Calc. C % 60.14; H % 6.49; N % 6.68 Fnd. C % 60.38; H % 6.54; N % 6.62

EXAMPLE 2

Preparation of N-[(N-allyl-2-pyrrolidinyl)methyl]-1-methoxy-4-cyano-2-naphthamide.

1. Preparation of 1-methoxy-4-cyano-2-naphthoic acid methyl ester.

1.16 g (432 mmol) of 1-methoxy-4-aminonaphthoic acid methyl ester are dissolved in 10 ml of 3N HCl. 3 ml of an aqueous solution of 0.415 g (1.2 eq) of sodium nitrite are added dropwise at 0° C. The reaction mixture is stirred for 30 min at 0° C. The mixture is then neutralised to pH 4 with sodium acetate. A solution of KCN (0.7 g) in water (6 ml) is prepared at the same time, CuCN (0.43 g) is added, this solution is maintained at 0° C. and the diazonium solution is added dropwise. The reaction is left for 2 h at 5° C. and the temperature is then allowed to rise. The precipitate obtained is filtered off and the product is purified by chromatography, using an ethyl acetate/hexane mixture as eluent, to recover 500 mg of the compound of the title—M.p. 92° C., IR 2200 $cm^{-1}$ (Yield=70%).

2. Preparation of 1-methoxy-4-cyano-2-naphthoic acid.

The 1-methoxy-4-cyano-2-naphthoic acid methyl ester obtained in 1 (500 mg, 2 mmol) and potassium bicarbonate (0.3 g, 1.5 eq) are brought to reflux for 24 h in 25 ml of methanol. The methanol is evaporated off and the residue is taken up in water and acidified with dilute hydrochloric acid. The mixture is extracted with ethyl acetate, and the organic phase is washed with water, dried and evaporated. 420 mg of the compound of the title are recovered in the form of a solid—M.p. 186° C., IR 2200 $cm^{-1}$ (Yield=92%).

3. Preparation of (N-tert-butoxycarbonylaminomethyl)-N-benzylpyrrolidine (Compound V).

3.42 g (18 mmol) of 2-aminomethyl-N-benzylpyrrolidine (Compound IV) dissolved in 100 ml of tetrahydrofuran (THF) are introduced into a 250-ml roundbottomed flask. A solution of di-tert-butyl dicarbonate dissolved in 30 ml of THF is added dropwise. The mixture is stirred at room temperature overnight. It is concentrated under vacuum, the residue formed is taken up in water and the mixture is then extracted with ether. The organic phase is dried and then evaporated. The residue is purified by chromatography on a silica column, using a hexane/ether mixture as eluent, to recover 5 g of the Compound V of the title (Yield=95%).

4. Preparation of 2-(N-tert-butoxycarbonylaminomethyl)-pyrrolidine (Compound VI).

The mixture of the Compound V (5 g, 0.017 mol) in methanol (125 ml) is brought to reflux for 2 h in the presence of 10% Pd/C (540 mg) and ammonium formate (5.69 g). The mixture is cooled and the catalyst is filtered off. The methanol is evaporated off and the residue is taken up in saturated potassium carbonate solution. The mixture is then extracted with ether and the organic phase is dried and concentrated under vacuum to obtain 3.7 g of the Compound V of the title (Yield=99%), which is used without further treatment for the following reaction.

5. Preparation of 2-(N-tert-butoxycarbonylaminomethyl)-N-allylpyrrolidine (Compound VII).

A mixture of the Compound (VI) (3.68 g, 0.017 mol), sodium bicarbonate (1.51 g, 0.018 mol), allyl bromide (1.55 g, 0.018 mol) and ethanol (170 ml) is heated to reflux for 10 h. It is evaporated and the residue is taken up with water. The mixture is then extracted with ether, the organic phase is dried and evaporated and the residue is purified on a silica column, using ethyl acetate as eluent, to recover 2.27 g of an oil (Compound VII, Yield=55%).

6. Preparation of 2-aminomethyl-N-allylpyrrolidine (Compound VIII).

A mixture of the Compound (VII) (1 g, 4.16 mmol), acetic acid (33 ml) and concentrated hydrochloric acid (11 ml) is stirred at room temperature for 1 h. It is evaporated, the residue is taken up several times with isopropanol and the mixture is then evaporated under vacuum. The residue is then dissolved in methanol, and triethylamine (0.58 ml, 4.16 mmol) is added. The methanol is evaporated off, the residue is taken up with ether and the organic phase is filtered, dried and concentrated to obtain 590 mg of the compound of the title (Yield=90%).

7. Preparation of N-[(N-allyl-2-pyrrolidinyl)methyl]-1-methoxy-4-cyano-2-naphthamide.

1-Methoxy-4-cyano-2-naphthoic acid (360 mg, 1.58 mmol) obtained in 2, in acetone (8 ml) is introduced into a 25-ml three-necked flask under argon. Triethylamine is added and the mixture is cooled to −15° C. Ethyl chloroformate (0.26 ml, 1.2 eq) dissolved in acetone (3 ml) is then added dropwise. The mixture is stirred for 30 min at −15° C. Triethylamine (0.26 ml) is added, followed by the dropwise addition of the hydrochloride of 2-aminomethyl-N-allylpyrrolidine (Compound VIII) dissolved in acetone (3 ml). The reaction medium is allowed to return to room temperature. The precipitate obtained is filtered off and the acetone is evaporated off. The residue is taken up in water, the mixture is extracted with ethyl acetate and the organic phase is dried and evaporated. The residue is purified by chromatography on a silica column, using a 90:10 ethyl acetate/methanol mixture as eluent, to obtain 210 mg of the compound of the title—M.p. 93° C. (38% yield).

Analysis: $C_{21}H_{23}N_3O_2$ Calc. C % 72.02; H % 6.80; N % 12.09 Found C % 72.18; H % 6.63; N % 12.02

EXAMPLE 3

4-Cyano-N-[(N-butyl-2-pyrrolidinyl)methyl]-1-methoxy-2-naphthamide.

1-Methoxy-4-cyano-2-naphthoic acid (227 μg, 1 mmol) in acetone (5 ml) is introduced into a 25-m) three-necked flask under argon. Triethylamine (0.17 ml) is added and the mixture is cooled to −15° C. Ethyl chloroformate (0.1 ml) dissolved in acetone (2 ml) is added dropwise. The mixture is left stirring for 30 min at −15° C. 2-Methylamino-N-butylpyrrolidine (164 mg, 1.05 mmol) dissolved in acetone (2 ml) is added. The mixture is left at room temperature. The triethylamine hydrochloride formed is filtered off, the acetone is evaporated off, the acetone is evaporated off, the residue is taken up in water and the mixture is extracted with ethyl acetate. The ethyl acetate phase is washed with water. It is dried and evaporated to obtain an oil, which crystallises. The product is purified by chromatography on a silica column (AcOEt/MeOH, 80:20). It is recrystallised in hexane to obtain the compound of the title (210 mg, 57%, m.p. 90° C.).

Analysis $C_{22}H_{27}N_3O_2$ Found C % 72.37; H % 6.63; N % 12.00; Calc. C % 72.29; H % 7.47; N % 11.49.

EXAMPLES 4 to 42

In the list which follows, a number of other compounds of formula (I) according to the invention, which were prepared according to the procedures described in the Examples 1 and 2, have been collated. In all cases, the results of the analyses and the NMR spectra confirmed the structure of the compounds.

EXAMPLE 4

N-[(N-Ethyl-2-pyrrolidinyl)methyl]-1-methoxy-2-naphthamide.

$C_{19}H_{25}N_2O_3$, M.p. 85° C.

EXAMPLE 5

4-Amino-N-[(N-ethyl-2-pyrrolidinyl)methyl]-1-methoxy-2-naphthamide dihydrochloride.

$C_{19}H_{25}N_3O_2,2HCl, H_2O$, M.p. 207° C.

EXAMPLE 6

4-Nitro-N-[(N-ethyl-2-pyrrolidinyl)methyl]-1-methoxy-2-naphthamide.

$C_{19}H_{23}N_3O_4$, M.p. 98° C.

EXAMPLE 7

N-[(N-Ethyl-2-pyrrolidinyl)methyl]-1,4-dimethoxy-2-naphthamide hydrochloride.

$C_{20}H_{27}ClN_2O_3$, M.p. 158° C.

EXAMPLE 8

4-Chloro-N-[(N-ethyl-2-pyrrolidinyl)methyl]-1-methoxy-2-naphthamide hydrochloride.

$C_{19}H_{23}BrN_2O_2,HCl, H_2O$, M.p. 188° C.

EXAMPLE 9

4-Bromo-N-[(N-ethyl-2-pyrrolidinyl)methyl]-1-methoxy-2-naphthamide hydrochloride.

$C_{19}H_{23}BrN_2O_2,HCl,H_2O$, M.p. 194° C.

EXAMPLE 10

4-Methylsulphonylamino-N-[(N-ethyl-2-pyrrolidinyl)methyl]-1-methoxy-2-naphthamide hydrochloride.

$C_{20}H_{27}N_3O_4S,HCl$, M.p. 229° C.

EXAMPLE 11

N-[(N-Benzyl-2-pyrrolidinyl)methyl]-1-methoxy-2-naphthamide hydrochloride.

$C_{24}H_{26}N_2O_2,HCl$, M.p. 145° C.

EXAMPLE 12

4-Nitro-N-[(N-benzyl-2-pyrrolidinyl)methyl]-1-methoxy-2-naphthamide.

$C_{24}H_{25}N_3O_4$, M.p. 123° C.

EXAMPLE 13

4-Chloro-N-[(N-benzyl-2-pyrrolidinyl)methyl]-1-methoxy-2-naphthamide.

$C_{24}H_{25}N_2O_2Cl$, M.p. 102° C.

EXAMPLE 14

4-Chloro-N-[(N-propyl-2-pyrrolidinyl)methyl]-1-methoxy-2-naphthamide.

$C_{20}H_{25}N_2O_2Cl$, M.p. 62° C.

EXAMPLE 15

4-Bromo-N-[(N-cyclopropylmethyl-2-pyrrolidinyl)methyl]-1-methoxy-2naphthamide.

$C_{21}H_{25}N_2O_2Br$, M.p. 86° C.

EXAMPLE 16

4-Chloro-N-[(N-allyl-2-pyrrolidinyl)methyl]-1-methoxy-2naphthamide.

$C_{20}H_{23}N_2O_2Cl$, M.p. 68° C.

EXAMPLE 17

4-Nitro-N-[(N-allyl-2-pyrrolidinyl)methyl-1-methoxy-2-naphthamide.

$C_{20}H_{23}N_3O_4$, M.p. 90° C.

EXAMPLE 18

4-Cyano-N-[(N-ethyl-2-pyrrolidinyl)methyl]-1-methoxy-2-naphthamide.

$C_{20}H_{23}N_3O_2$, M.p. 84° C.

EXAMPLE 19

4-Cyano-N-{[N-(3-butenyl)-2-pyrrolidinyl]methyl}-1-methoxy-2-naphthamide.

$C_{22}H_{25}N_3O_2$, M.p. 115° C.

EXAMPLE 20

4-Cyano-N-[(N-pentyl-2-pyrrolidinyl)methyl]-1-methoxy-2-naphthamide.

$C_{23}H_{29}N_3O_2$, M.p. 74° C.

EXAMPLE 21

4-Cyano-N-{[N-(4-pentenyl)-2-pyrrolidinyl]methyl{-1-methoxy-2-naphthamide.

$C_{23}H_{27}N_3O_2$, M.p. 66° C.

EXAMPLE 22

1,5-Dimethoxy-N-[(N-ethyl-2-pyrrolidinyl)methyl]-2-naphthamide hydrochloride.

$C_{20}H_{27}N_2ClO_3$, M.p. 185° C.

EXAMPLE 23

1,5-Dimethoxy-N[(N-butyl-2-pyrrolidinyl)methyl]-2-naphthamide hydrochloride.

$C_{22}H_{31}N_2ClO_3$, M.p. 131° C.

EXAMPLE 24

4-Bromo-N-[(N,N-diethylamino)ethyl]-1-methoxy-2-naphthamide.

$C_{18}H_{23}BrN_2O_2$, M.p. 54° C.

EXAMPLE 25

4-Bromo-N-[(morpholino)ethyl]-1-methoxy-2-naphthamide.

$C_{18}H_{21}N_2BrO_3$, M.p. 87° C.

EXAMPLE 26

4-Bromo-N-(N-butyl-4-piperidyl)-1-methoxy-2-naphthamide.

$C_{21}H_{27}N_2BrO_2$, M.p. 121° C.

EXAMPLE 27

4-Bromo-N-(N-benzyl-4-piperidyl)-1-methoxy-2-naphthamide.

$C_{24}H_{25}N_2O_2Br$, M.p. 157° C.

EXAMPLE 28

4-Nitro-N-[(morpholino)ethyl]-1-methoxy-2-naphthamide.

$C_{18}H_{21}N_3O_5$, M.p. 92° C.

EXAMPLE 29

4-Nitro-N-[(N-butyl-2-pyrrolidinyl)methyl]-1,5-dimethoxy-2-naphthamide hydrochloride.

$C_{22}H_{30}N_3O_5Cl$ 1.5 $H_2O$, M.p. 102° C.

EXAMPLE 30

4-Nitro-N-(N-butyl-4-piperidyl)-1-methoxy-2-naphthamide.

$C_{21}H_{27}N_3O_4$, M.p. 134° C.

EXAMPLE 31

4-Nitro-N-[(N,N-diethylamino)ethyl]-1-methoxy-2-naphthamide.

$C_{18}H_{23}N_3O_4$, M.p. 84° C.

EXAMPLE 32

4-Bromo-N-[(N,N-dibutylamino)ethyl]-1-methoxy-2-naphthamide hydrochloride.

$C_{22}H_{32}N_2O_2BrCl$, M.p. 106° C.

EXAMPLE 33

4-Bromo-N-[(N-ethyl-2-pyrrolidinyl)methyl]-1-butoxy-2-naphthamide.

$C_{22}H_{29}N_2O_2Br$, M.p. 92° C.

EXAMPLE 34

4-Nitro-N-[(N-ethyl-2-pyrrolidinyl)methyl]-1,5-dinitro-2-naphthamide.

$C_{20}H_{35}N_3O_5$, M.p. 57° C.

EXAMPLE 35

4-Bromo-N-(N-butyl-4piperidyl)-1-allyloxy-2-naphthamide.

$C_{23}N_2N_2O_2Br$, M.p. 72° C.

EXAMPLE 36

4-Bromo-N-[(morpholino)ethyl]-1-allyloxy-2-naphthamide hydrochloride.

$C_{20}H_{24}N_2O_3BrCl$, M.p. 93° C.

EXAMPLE 37

1,4-Dimethoxy-N-(N-butyl-4-piperidyl)-2-naphthamide hydrochloride.

$C_{22}H_{31}N_2O_3Cl$, M.p. 137° C.

EXAMPLE 38

4-Bromo-N-[(morpholino)ethyl]-1-butoxy-2-naphthamide hydrochloride.

$C_{21}H_{28}N_2O_3BrCl$, M.p. 149° C.

EXAMPLE 39

4-Bromo-N-[(N-ethyl-2-pyrrolidinyl)methyl]-1-cyclopentyloxy-2-naphthamide hydrochloride.

$C_{23}H_{30}N_2O_2BrCl$, M.p. 138° C.

EXAMPLE 40

4-Nitro-N-[(N,N-dibutylamino)ethyl]-1-methoxy-2-naphthamide hydrochloride.

$C_{22}H_{32}N_3O_4Cl$, M.p. 113° C.

EXAMPLE 41

4-Bromo-N-[(2-pyrrolidinyl)ethyl]-1-methoxy-2-naphthamide.

$C_{18}H_{21}N_2O_2Br$, M.p. 91° C.

EXAMPLE 42

4-Cyano-N-[(N,N-dibutylamino)ethyl]-1-methoxy-2-naphthamide hydrochloride.

$C_{23}H_{32}N_3O_2Cl$, M.p. 86° C.

The compounds of formula (I) according to the invention were subjected to pharmacological tests which enabled their antidopaminergic properties to be demonstrated.

Measurement of affinity for the dopamine $D_3$ receptor.

The inhibition constants for the binding of [$^{125}$I]iodosulpiride to the $D_3$ receptor were measured as described in the French Patent Application filed by INSERM on 6th Nov. 1990 under No. 90/13731. The results obtained have been correlated in the table which follows. It is apparent that the compounds of the invention have a high affinity for the $D_3$ receptor, which, in the case of some of the compounds, is better than that measured for haloperidol and sulpiride described previously.

Antidopaminergic activity in vivo.

The capacity to bring about a blockade of the dopamine receptors in vivo was evaluated for some of the compounds according to the invention. The tests used were the antagonism of stereotyped sniffing and rearing induced by apomorphine in mice. These tests have been described by Protais et al. (Psychopharmacology, 1976, 50:1–6) and by Vasse et al. (Naunyn Schmiedeberg's Arch. Pharmacol., 1985, 329:108–116). As an example, the $ID_{50}$ values of the compound of Example 8 for the antagonism for rearing and sniffing are 0.16 mg/kg i.p. and 0.42 mg/kg i.p., respectively, indicating that the compound readily crosses the blood-brain barrier and brings about an effective blockade of the dopamine receptors.

The results obtained in the pharmacological tests, whether performed in vivo or in vitro, shows that the compounds of the invention are new dopamine antagonists which are active with respect to the dopamine $D_3$ receptor. The selective expression of this receptor in the limbic regions of the brain, which are capable of being affected in various psychiatric disorders, together with the high affinity of most neuroleptic or antipsychotic agents for this receptor, suggest that blockade of the $D_3$ receptor plays a crucial part in the treatment of these disorders.

The present invention hence also relates to a medicinal product which is a dopamine antagonist by blockade of the $D_3$ receptor, containing as active principle at least one of the compounds of the general formula (I), intended for use as an antipsychotic, antidepressant, psychostimulatory or anti-autistic agent, an agent for treating Parkinson's disease or alternatively an antihypertensive agent.

The invention also relates to the use of these compounds for the preparation of these medicinal products, comprising incorporation of the compound in an oral or parenteral vehicle or excipient, including their production in the form of individual doses.

The compounds of formula (I) according to the invention may be administered orally or parenterally, in the form of pharmaceutical compositions containing the active principle in combination with a pharmaceutically acceptable vehicle or excipient. The compounds of the invention are active at daily doses of between 0.01 and 10 mg/kg.

TABLE

INHIBITION CONSTANTS OF VARIOUS COMPOUNDS OF THE INVENTION FOR BINDING TO THE HUMAN $D_3$ DOPAMINERGIC RECEPTOR, COMPARED WITH THAT OF HALOPERIDOL AND OF SULPIRIDE.

| COMPOUND | $K_i$ VALUE (nM) |
|---|---|
| Example | |
| no. 1 | 0.24 |
| no. 2 | 0.51 |
| no. 4 | 35 |
| no. 6 | 0.30 |
| no. 8 | 0.26 |
| no. 11 | 91 |
| no. 12 | 1.7 |
| no. 13 | 4.7 |
| no. 17 | 0.35 |
| Haloperidol | 2.9 |
| Sulpiride | 20 |

We claim:
1. Naphthamide derivatives of the general formula (I).

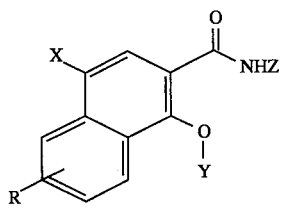

where
X: represents either a hydrogen atom, or a chlorine or bromine atom, or an amino or aminoalkyl group a sulphamoyl group, thiocyanate, alkylthio, alkylsulphi-nyl or alkylsulphonyl, or a methoxy group, or a nitro group, or a cyano group,;

Y: represents an alkyl or alkenyl residue;

Z: represents 2 methyl-N-alkyl-pyrrolidine or 2-ethylpyrrolidine;

R: a hydrogen or $OCH_3$ substituent.

2. Substituted 1-methoxy-2-naphthamide derivatives according to claim 1 of the general formula (Ia)

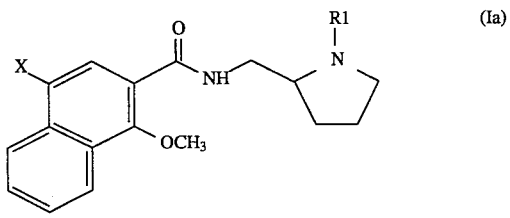

where X represents a hydrogen atom, chlorine or bromine, an amino or aminoalkyl group, an aminosulphamoyl group, a methoxy group, a nitro group or alternatively a cyano group, R1 represents alkyl, as well as their addition salts with physiologically acceptable acids.

3. Derivatives of formula (Ia) according to claim 2, characterised in that X represents a hydrogen atom, a chlorine or fluorine atom, an amino, nitro or cyano group or alternatively a methoxy group, and R1 represents an ethyl, propyl or butyl radical.

4. Derivatives of formula (I) according to claim 1, characterised in that they are chosen from the group consisting of:

N-[(1-Butyl-2-pyrrolidinyl)methyl]-1-methoxy-4-bromo-2-naphthamide, optionally in hydrochloride form,

[N-[(N-Allyl-2-pyrrolidinyl)methyl]-1methoxy-4-cyano-2-naphthamide,]

N-[(N-Ethyl-2-pyrrolidinyl)methyl]-1-methoxy-2-naphthamide,

4-Amino-N-[(N-ethyl-2-pyrrolidinyl)methyl]-1-methoxy-2-naphthamide, optionally in dihydrochloride form, 4-Nitro-N](N-ethyl-2-pyrrolidinyl)methyl]-1-methoxy-2-naphthamide, N-[(N-Ethyl-2-pyrrolidinyl)methyl]-1,4-dimethoxy-2-naphthamide, optionally in hydrochloride form, 4-Chloro-N-[(N-ethyl-2-pyrrolidinyl)methyl]-1-methoxy-2-naphthamide, optionally in hydrochloride form, 4-Bromo-N-[(N-ethyl-2-pyrrolidinyl)methyl]-1-methoxy-2-naphthamide, optionally in hydrochloride form, 4-Methylsulphonylamino-N-[(N-ethyl-2-pyrrolidinyl)methyl]-1-methoxy-2-naphthamide, optionally in hydrochloride form,

[N-[(N-Benzyl-2-pyrrolidinyl)methyl]-1-methoxy-2-naphthamide, optionally in hydrochloride form,]

[4-Nitro-N-[(N-benzyl-2-pyrrolidinyl)methyl]-1-methoxy-2-naphthamide,]

[4-Chloro-N-[(N-benzyl-2-pyrrolidinyl)methyl]-1-methoxy-2-naphthamide,]

4-Chloro-N-[(N-propyl-2-pyrrolidinyl)methyl]-1-methoxy-2-naphthamide,

[4-Bromo-N-[(N-cyclopropylmethyl-2-pyrrolidinyl)methyl]-1-methoxy-2-naphthamide, 4-Chloro-N-[(N-allyl-2-pyrrolidinyl)methyl]-1-methoxy-2-naphthamide, methoxy-2-naphthamide, 4-Cyano-N-[(N-ethyl-2-pyrrolidinyl)methyl]-1-methoxy-2-naphthamide, 4-Cyano-N-[(N-butyl-2-pyrrolidinyl)methyl]-1-methoxy-2-naphthamide

[4-Cyano-N-{[N-(3-butenyl)-2-pyrrolidinyl]methyl)-1-methoxy-2-naphthamide,]

4-Cyano-N-[(N-pentyl-2-pyrrolidinyl)methyl]-1-methoxy-2-naphthamide,
[4-Cyano-N-{[N-4-pentenyl)-2-pyrrolidinyl]methyl)-1-methoxy-2-naphthamide,]
1,5-Dimethoxy-N-[(N-ethyl-2-pyrrolidinyl)methyl]-2-naphthamide hydrochloride,
1,5-Dimethoxy-N[(N-butyl-2-pyrrolidinyl)methyl]-2-naphthamide hydrochloride,
[4-Bromo-N-[(N,N-diethylamino)ethyl]-1-methoxy-2-naphthamide,
4-Bromo-N-[(morpholino)ethyl]-1-methoxy-2-naphthamide,
4-Bromo-N-(N-butyl-4-piperidyl)-1-methoxy-2-naphthamide,
4-Bromo-N-(N-benzyl-4-piperidyl)-1-methoxy-2-naphthamide,
4-Nitro-N-[(morpholino)othyl]-1-mothoxy-2-naphthamide,]
4-Nitro-N-[(N-butyl-2-pyrrolidinyl)methyl]-1,5-dimethoxy-2-naphthamide hydrochloride,
[4-Nitro-N-(N-butyl-4-piperidyl)-1-methoxy-2-naphthamide,
4-Nitro-N-[(N,N-diethylamino)ethyl]-1-methoxy-2-naphthamide,
4-Bromo-N-[(N,N-dibutylamino)ethyl]-1-methoxy-2-naphthamide hydrochloride,]
4-Bromo-N-[(N-ethyl-2-pyrrolidinyl)methyl]-1-butoxy-2-naphthamide,
4-Nitro-N-[(N-ethyl-2-pyrrolidinyl)methyl]-1,5-dinitro-2-naphthamide, [
4-Bromo-N-(N-butyl-4-piperidyl)-1-allyloxy-2-naphthamide,
4-Bromo-N-[(morpholino)ethyl]-1-allyloxy-2-naphthamide hydrochloride,
1,4-Dimethoxy-N-(N-butyl-4-piperidyl)-2-naphthamide hydrochloride,
4-Bromo-N-[(morpholino)ethyl]-1-butoxy-2-naphthamide hydrochloride,
4-Bromo-N-[(N-ethyl-2-pyrrolidinyl)methyl]-1-cyclopentyloxy-2-naphthamide hydrochloride,
4-Nitro-N-[(N,N-dibutylamino)ethyl]-1-methoxy-2-naphthamide hydrochloride,]
4-Bromo-N-[(2-pyrrolidinyl)ethyl]-1-methoxy-2-naphthamide,
[4-Cyano-N-[(N,N-dibutylamino)ethyl]-1-methoxy-2-naphthamide hydrochloride.]

5. Pharmaceutical composition, characterised in that it contains at least one compound according to one of claims 1 to 4, in combination with a pharmaceutically acceptable vehicle or excipient.

6. Medicinal product which is a dopamine antagonist by blockade of the $D_3$ receptor, characterised in that it contains at least one of the compounds of formula (I) according to one of claim 1 to 4.

7. A pharmaceutical composition useful as an antipsychotic, psychostimulatory, anti-autistic or antidepressant agent, an agent for treating Parkinson's disease or an antihypertensive agent containing a compound according to claim 1 in combination with a pharmaceutically acceptable vehicle or excipient.

* * * * *

UNITED STATES PATENT AND TRADEMARK OFFICE
CERTIFICATE OF CORRECTION

PATENT NO. : 5,498,628
DATED : March 12, 1996
INVENTOR(S) : ROGNAN et al.

Page 1 of 2

It is certified that error appears in the above-indentified patent and that said Letters Patent is hereby corrected as shown below:

4. Derivatives of formula (I) according to claim 1, characterised in that they are chosen from the group consisting of:
N-[(1-Butyl-2-pyrrolidinyl)methyl]-1-methoxy-4-bromo-2-naphthamide, optionally in hydrochloride form,
N-[(N-Ethyl-2-pyrrolidinyl)methyl]-1-methoxy-2-naphthamide,
4-Amino-N-[(N-ethyl-2-pyrrolidinyl)methyl]-1-methoxy-2-naphthamide, optionally in dihydrochloride form,
4-Nitro-N[(N-ethyl-2-pyrrolidinyl)methyl]-1-methoxy-2-naphthamide,
N-[(N-Ethyl-2-pyrrolidinyl)methyl]-1,4-dimethoxy-2-naphthamide, optionally in hydrochloride form,
4-Chloro-N-[(N-ethyl-2-pyrrolidinyl)methyl]-1-methoxy-2-naphthamide, optionally in hydrochloride form,
4-Bromo-N-[(N-ethyl-2-pyrrolidinyl)methyl]-1-methoxy-2-naphthamide, optionally in hydrochloride form,
4-Methylsulphonylamino-N-[(N-ethyl-2-pyrrolidinyl)methyl]-1-methoxy-2-naphthamide, optionally in hydrochloride form,
4-Chloro-N-[(N-propyl-2-pyrrolidinyl)methyl]-1-methoxy-2-naphthamide,
4-Chloro-N-[N-allyl-2-pyrrolidinyl)methyl]-1-methoxy-2-naphthamide, methoxy-2-naphthamide,
4-Cyano-N-[(N-ethyl-2-pyrrolidinyl)methyl]-1-methoxy-2-naphthamide,
4-Cyano-N-[(N-butyl-2-pyrrolidinyl)methyl]-1-methoxy-2-naphthamide,
4-Cyano-N-[(N-pentyl-2-pyrrolidinyl)methyl]-1-methoxy-2-naphthamide,
1,5-Dimethoxy-N-[(N-ethyl-2-pyrrolidinyl)methyl]-2-naphthamide hydrochloride,
1,5-Dimethoxy-N[(N-butyl-2-pyrrolidinyl)methyl]-2-naphthamide hydrochloride,
4-Nitro-N-[(N-butyl-2-pyrrolidinyl)methyl]-1,5-dimethoxy-2-naphthamide hydrochloride,
4-Bromo-N-[(N-ethyl-2-pyrrolidinyl)methyl]-1-butoxy-2-naphthamide,
4-Nitro-N-[(N-ethyl-2-pyrrolidinyl)methyl]-1,5-dinitro-2-naphthamide,

UNITED STATES PATENT AND TRADEMARK OFFICE
CERTIFICATE OF CORRECTION

PATENT NO. : 5,498,628
DATED : March 12, 1996
INVENTOR(S) : ROGNAN et al.

It is certified that error appears in the above-indentified patent and that said Letters Patent is hereby corrected as shown below:

4-Bromo-N-[(2-pyrrolidinyl)ethyl]-1-methoxy-2-naphthamide.

Signed and Sealed this

Eighteenth Day of February, 1997

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO. : 5,498,628
DATED : March 12, 1996
INVENTOR(S) : Rognan et al

It is certified that error appears in the above-indentified patent and that said Letters Patent is hereby corrected as shown below:

Title page: item [73] under "Institut National de la Sante et de la Recherche Medicale, Paris, France" insert --Societe Civile BIOPROJET, Paris, France--.

Signed and Sealed this

Twenty-eighth Day of October, 1997

*Attest:*

BRUCE LEHMAN

*Attesting Officer*    Commissioner of Patents and Trademarks